United States Patent
Benvenuti et al.

(10) Patent No.: US 6,670,434 B2
(45) Date of Patent: Dec. 30, 2003

(54) CATALYTIC COMPLEXES AND THEIR USE FOR POLYMERIZING ALPHA-OLEFINS

(75) Inventors: Federica Benvenuti, Brussels (BE); Philippe Francois, Court-Saint-Etienne (BE)

(73) Assignee: Solvay Polyolefins Europe-Belgium (Societe Anonyme), Brussels (BE)

( * ) Notice: Subject to any disclaimer, the term of this patent is extended or adjusted under 35 U.S.C. 154(b) by 0 days.

(21) Appl. No.: 10/147,886

(22) Filed: May 20, 2002

(65) Prior Publication Data

US 2003/0018147 A1 Jan. 23, 2003

(30) Foreign Application Priority Data

May 23, 2001 (BE) .......................... 2001/0353

(51) Int. Cl.$^7$ .............. C08F 4/44; B01J 31/18
(52) U.S. Cl. .............. 526/171; 526/172; 502/155; 502/167
(58) Field of Search ............... 526/171, 172; 502/167, 155

(56) References Cited

FOREIGN PATENT DOCUMENTS

| EP | 1 125 952 A1 | 8/2001 |
|---|---|---|
| EP | 1 125 979 A1 | 8/2001 |
| WO | WO 99/12981 | 3/1999 |
| WO | WO 99/46302 | 9/1999 |
| WO | WO 99/46303 | 9/1999 |
| WO | WO/50318 | 10/1999 |
| WO | WO 99/62967 | 12/1999 |
| WO | WO 32641 | 6/2000 |
| WO | WO 00/55216 | 9/2000 |
| WO | WO 00/69869 | 11/2000 |
| WO | WO 00/69923 | 11/2000 |

OTHER PUBLICATIONS

Gibson et al., Oligomerization of Ethylene by Bis(imino)pyridyliron and –cobalt Complexes, Chem. Eur. J. 2000, 6 No. 12, p. 2221–31.*

Geroge J.P. Britovesek, et al., *Oligomerisation of Ethylene by Bis(imino)pyridyliron and –cobalt Complexes*, Chemical Eur. J., 6, No. 12, 2000, pp. 2221–2231.

Jaioming Quiu, et al., *Rapid Report A New Iron–Based Catalyst for Ethylen Polymerization*, Polymer International, (2000) 49, pp. 5–7.

Shiyou Huagong, et al., XP–00218449—English Abstract, CA Database Accession No. 133:335517, (2000), 29 (6), 425–427.

* cited by examiner

Primary Examiner—Robert Harlan
(74) Attorney, Agent, or Firm—Oblon, Spivak, McClelland, Maier & Neustadt, P.C.

(57) ABSTRACT

A complex of a transition metal complying with the general formula (I)

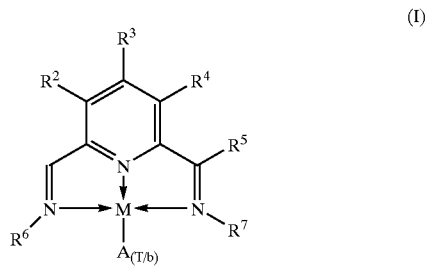

in which
  M is a transition metal of groups 6 to 12,
  T is the oxidation state of M,
  each A, which may be identical with or differ from each other, is an atom or an atomic grouping bonded covalently or ionically to the transition metal M,
  b is the valency of A,
  each $R^1$, $R^2$, $R^3$, $R^4$ and $R^5$ is independently a hydrogen atom, an unsubstituted or substituted hydrocarbon group, an unsubstituted or substituted heterohydrocarbon group, or an inert functional group,
  $R^6$ and $R^7$ are, independently of one another, a polynuclear aromatic hydrocarbon group containing at least two condensed benzene nuclei, substituted with at least one hydrocarbon group.

19 Claims, No Drawings

CATALYTIC COMPLEXES AND THEIR USE FOR POLYMERIZING ALPHA-OLEFINS

BACKGROUND OF THE INVENTION

The present invention relates to complexes of 2,6-pyridinebis(imines) with transition metals and their use for polymerizing alpha-olefins.

DISCUSSION OF THE BACKGROUND

It is known that alpha-olefins can be polymerized by means of complexes comprising a transition metal and a tridentate ligand, and an aluminoxane. Patent application WO 99/62967 describes the copolymerization of ethylene with the aid of complexes of iron with 2,6-pyridinebis (imines). However, the catalytic complexes described in that application do not efficiently incorporate propylene during the manufacture of copolymers of ethylene. Patent application WO 99/12981, Britovsek et al. (Chem. Eur., 2000, 6(12), 2221) and Qiu et al. (Polym. Int., 2000, 49(1), 5) report the syntheses of {2,6-bis[1-(1-naphthylimino) methyl]-pyridine-$\kappa^3$: N,N',N"}$FeCl_2$ and of {2,6-bis[1-(1-naphthylimino)ethyl]pyridine-$\kappa^3$: N,N',N"}$FeCl_2$ and their use for polymerizing ethylene in the presence of methylaluminoxane (MAO). However, the catalytic activity of these complexes and the molecular weights of the polyethylenes obtained are low.

We have now found complexes of a transition metal with 2,6-pyridinebis(imines) for polymerizing alpha-olefins where these do not have the abovementioned disadvantages.

SUMMARY OF THE INVENTION

The present invention therefore provides complexes of a transition metal complying with the general formula (I) in which

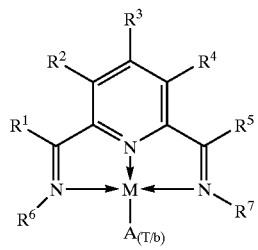

(1)

M is a transition metal of groups 6 to 12,
T is the oxidation state of M,
each A, which may be identical with or differ from each other, is an atom or an atomic grouping bonded covalently or ionically to the transition metal M,
b is the valency of A,
each $R^1$, $R^2$, $R^3$, $R^4$ and $R^5$ is independently a hydrogen atom, an unsubstituted or substituted hydrocarbon group, an unsubstituted or substituted heterohydrocarbon group, or an inert functional group,
$R^6$ and $R^7$ are, independently of one another, a polynuclear aromatic hydrocarbon group containing at least two condensed benzene nuclei, substituted with at least one hydrocarbon group.

DETAILED DESCRIPTION OF THE INVENTION

All the references to the Periodic Table of the Elements refer to the version published in CRC Handbook of Chemistry and Physics, 77th Edition, 1996/97; the notation utilized is the new IUPAC notation for the groups.

An "inert functional group" is understood to be an atomic grouping which is not an unsubstituted or substituted (hetero) hydrocarbon group, this group being inert under the conditions of the process using the complex of the present invention, and not coordinating with the transition metal M. Examples which may be mentioned of inert functional groups are halogen atoms and ethers of formula OR in which R is an unsubstituted or substituted hydrocarbon group.

Preferred complexes are those complying with the general formula (I) in which M is Fe, Cr, Co, Ru or Mn. Particular preference is given to Fe. Suitable complexes are those complying with the general formula (I) in which T is 2.

Each A is generally selected from halogen atoms, sulphates, nitrates, thiolates, thiocarboxylates, $BF_4$—, $PF_6$—, hydrogen atoms, hydrocarbon oxides, carboxylates, unsubstituted or substituted hydrocarbon groups, and heterohydrocarbon groups. Preferred complexes are those complying with the general formula (I) in which A is a halogen atom or a linear or branched alkyl group containing from 1 to 8 carbon atoms. Preference is very particularly given to complexes of the formula (I) in which A is a halogen atom.

Suitable complexes of the invention are those complying with the general formula (I) in which $R^1$, $R^2$, $R^3$, $R^4$ and $R^5$ are independently a hydrogen atom or a linear or branched alkyl group containing from 1 to 6 carbon atoms. The complexes in which $R^1$ and $R^5$ are independently a linear or branched alkyl group containing from 1 to 6 carbon atoms are particularly preferred, since they have high activity.

$R^6$ and $R^7$ are preferably selected independently of each other from groups complying with the formulae (II) or (III) below: in which $R^8$ to $R^{21}$ are independently hydrogen atoms or hydrocarbon groups, such

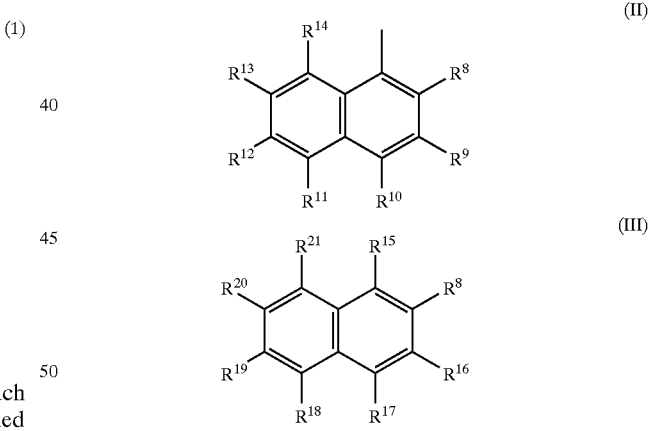

that at least two thereof can form a ring, with the proviso that at least one of the groups selected from $R^8$ to $R^{14}$ is not a hydrogen atom.

The groups (II) in which $R^{11}$ and $R^{12}$, $R^{12}$ and $R^{13}$, or $R^{13}$ and $R^{14}$ together form an unsubstituted or substituted benzene nucleus advantageously give alpha-olefin polymers having high molecular weight. The groups (II) in which $R^{12}$ and $R^{13}$ together form an unsubstituted or substituted benzene nucleus are particularly suitable. The groups (II) in which at least one of the groups selected from $R^{12}$, $R^8$ and $R^9$ represents a linear or branched alkyl group containing from 1 to 8 carbon atoms are preferred because they generally give high catalytic activity. The groups (II) in which $R^8$ is a linear or branched alkyl group containing from 1 to 8 carbon atoms are particularly preferred. The groups (II) in which $R^{12}$ and $R^{13}$ together form an unsubstituted or substituted benzene nucleus and $R^8$ is a linear or branched alkyl group containing from 1 to 8 carbon atoms are particularly preferred because they usually permit alpha-olefin polymers having high molecular weight to be obtained with high activity.

The groups (III) in which $R^{18}$ and $R^{19}$, $R^{19}$ and $R^{20}$, or $R^{20}$ and $R^{21}$ together form an unsubstituted or substituted benzene nucleus usually give alpha-olefin polymers having high molecular weight. The groups (III) in which at least one of the groups selected from $R^{15}$ and $R^{16}$ is a linear or branched alkyl group containing from 1 to 8 carbon atoms are preferred because they generally give complexes having high catalytic activity. The groups (III) in which $R^{19}$ and $R^{20}$ together form an unsubstituted or substituted benzene nucleus and $R^{15}$ or $R^{16}$ is a linear or branched alkyl group containing from 1 to 8 carbon atoms advantageously permit alpha-olefin polymers having high molecular weight to be obtained with high activity.

It is preferable to use complexes in which $R^6$ and $R^7$ comply with formula (II). The complexes in which $R^1$ and $R^5$ are a linear or branched alkyl group containing from 1 to 6 carbon atoms, and $R^6$ and $R^7$ comply with the formula (II) in which $R^8$ is a linear or branched alkyl group containing from 1 to 8 carbon atoms are very particularly preferred. Examples which may be mentioned of abovementioned complexes are $\{2,6\text{-bis}[1\text{-}(2\text{-methyl-1-naphthylimino}) \text{methyl}]\text{pyridine-}\kappa^3\colon \text{N,N',N"}\}\text{FeCl}_2$, $\{2,6\text{-bis}[1\text{-}(1\text{-anthracenylimino})\text{methyl}]\text{pyridine-}\kappa^3\colon \text{N,N',N"}\}\text{—FeCl}_2$, $\{2,6\text{-bis}[1\text{-}(1\text{-anthracenylimino})\text{ethyl}]\text{pyridine-}\kappa^3\colon \text{N,N',N"}\}\text{FeCl}_2$ and $\{2,6\text{-bis}[1\text{-}(2\text{-methyl-1-naphthyl-imino}) \text{ethyl}]\text{pyridine-}\kappa^3\colon \text{N,N',N"}\}\text{FeCl}_2$.

The complexes of the invention are generally prepared by a first condensation step of Schiff-base type, using amine and unsubstituted or substituted 2,6-bis(carbonyl)pyridine, as described by Britovsek et al. in J. Am. Chem. Soc., 1999, 121, 8728 and Small et al. in J. Am. Chem. Soc., 1998, 120, 4049. This reaction is then followed by addition of the di(imino)pyridine thus obtained to a salt of the transition metal (M) in order to obtain a complex complying with the general formula (I). The condensation reaction is usually carried out by using 2 equivalents of amine to 1 equivalent of 2,6-bis(carbonyl)pyridine. The di(imino)pyridine obtained is preferably added to a halide of the transition metal (M). This complexation reaction may be followed by reaction of the complex obtained with a Grignard reagent of formula AMgBr, in which A is a linear or branched alkyl group containing from 1 to 8 carbon atoms.

The complexes of the invention may be used as catalysts for polymerizing alpha-olefins. The invention therefore also provides a process for polymerizing alpha-olefins by bringing at least one alpha-olefin into contact, under polymerizing conditions, with a catalytic system comprising (a) a complex of a transition metal from groups 6 to 12 in accordance with the invention and (b) at least one activator.

The activators are generally selected from organoaluminium compounds. Use is usually made of aluminoxanes or of trialkylaluminium compounds. The preferred aluminoxane is methylaluminoxane (MAO). The trialkylaluminium compounds are advantageously selected from trimethylaluminium (TMA), triethylaluminium (TEA), triisobutylaluminium (TIBAL), and mixtures of these.

The quantity of activator used in the process of the invention is generally such that the atomic ratio of aluminium to the transition metal (M) derived from the complex (a) is from 10 to 20 000. This ratio is preferably at least 30, more particularly at least 50. Good results are obtained when this ratio is at least 100. This ratio is usually not more than 10 000. Ratios of from about 200 to 6000 give particularly good results.

For the purposes of the present invention, alpha-olefins are understood to be terminally unsaturated olefins generally containing from 2 to 20 carbon atoms, preferably from 2 to 8 carbon atoms. Examples of alpha-olefins are ethylene, propylene, 1-butene, 1-pentene, 1-hexene and 1-octene. Besides the olefin, it is of course possible for another monomer copolymerizable with the olefin to be used in the process of the invention.

The polymerization process of the invention may be carried out continuously or batchwise, in accordance with any known process, in solution, or in suspension, or even in the gas phase. The polymerization process of the invention is advantageously carried out in suspension in the monomer or in one of the monomers, kept in the liquid state, or in a hydrocarbon diluent, generally selected from aliphatic hydrocarbons containing from 3 to 10 carbon atoms. The diluent is preferably selected from propane, isobutane, hexane, and mixtures of these.

In the process of the invention, the complex of the transition metal (a) is preferably mixed with the activator (b) before it comes into contact with the alpha-olefin. In one advantageous version of the process of the invention, only some of the activator may be used for mixing with the complex, the rest of the activator being introduced directly into the polymerization reactor, optionally in the presence of alpha-olefin. The quantity of activator used in precontact is generally such that the atomic ratio of the aluminium to the transition metal (M) derived from the catalytic complex (a) is from 1 to 10000. This ratio is preferably at least 10, more particularly at least 50. Good results are obtained when this ratio is at least 100. The quantity of activator is usually such that this ratio is not more than 5000. Ratios of from about 300 to 2000 give particularly good results.

The temperature at which the polymerization is carried out is generally from −20 to +150° C., typically from 20 to 115° C.

The total pressure at which the process of the invention is carried out is generally selected between atmospheric pressure and $100 \times 10^5$ Pa, more particularly between $5 \times 10^5$ and $55 \times 10^5$ Pa.

The polymerization process of the invention is advantageously applied to the manufacture of polymers of ethylene, and more particularly to the manufacture of homo- and copolymers of ethylene. Homopolymers of ethylene thus frequently have ethyl and/or butyl branching. The preferred copolymers are those of ethylene with another alpha-olefin containing from 3 to 8 carbon atoms. Particular preference is given to copolymers of ethylene with propylene, with 1-butene and/or with 1-hexene. In the case of copolymerization of ethylene with another alpha-olefin containing from 3 to 8 carbon atoms, the polymerization is preferably carried out in that alpha-olefin in the liquid state, and with a low concentration of ethylene, based on the concentration of alpha-olefin, in the polymerization medium.

The process of the invention can give alpha-olefin polymers with high catalytic activity and can manufacture alpha-olefin polymers of high molecular weight. It can also give branched polyethylenes, or copolymers of ethylene, and more particularly copolymers of ethylene which may contain up to 99% by weight of monomeric units derived from propylene. These polymers are therefore a supplementary subject-matter of the present invention.

EXAMPLES

The examples below serve to illustrate the invention. The methods for measuring the quantities mentioned in the examples and the meaning of the symbols used in these examples are explained below.

IR spectra were recorded on KBr pressings using a Perkin Elmer FTIR 1720X Fourier transform spectrometer. Proton nuclear magnetic resonance spectra ($^1$H NMR) were recorded using a Bruker AMX 500 NMR spectrometer operating at 500 MHz. The significance of the characteristics revealed by $^{13}$C NMR and IR for the compounds synthesized is explained in Spectroscopic Methods in Organic Chemistry, D. H. Williams & I. Fleming. The ethyl and butyl branching in the polyethylenes (expressed as number per 1000 carbon atoms), and the rate of incorporation of 1-hexene or of propylene in the copolymers of ethylene with 1-hexene or propylene, respectively, were determined by $^{13}$C NMR using the same spectrometer. In copolymers of ethylene with propylene, $E_xP_yE_zP_t$ is the molar fraction of triads of x monomeric units derived from ethylene (E) followed by y monomeric units derived from propylene (P) followed by z monomeric units derived from ethylene (E) followed by t monomeric units derived from propylene (P), where $0 \leq x \leq 3$, $0 \leq y \leq 3$, $0 \leq t \leq 3$, $0 \leq z \leq 3$, x+y+t+z=3, and where x, y, z and t are integers and where at least one of x, y, z and t is 0; the molar fractions of the triads are determined by $^{13}$C NMR following the method described by J. C. Randall in J. Macromol Sci, Rev. Macromol. Chem Phys., 1989, 29 (2&3), 201–317.

The melting points (mp) and the enthalpies of fusion (ΔHm) were determined by differential scanning calorimetry in accordance with the standard ISO 3146 (1997).

The symbols $C_2$ and $C_3$ have been utilized to indicate, respectively, the monomers ethylene and propylene and the monomeric units derived from ethylene and from propylene.

The weight-average (Mw) and number-average (Mn) molecular weights were obtained by steric exclusion chromatography starting with a 0.5 g/l solution of polymer in trichlorobenzene, by means of a Waters STYRAGEL® HMW 6E polystyrene column. The distribution of molecular weights is expressed by the ratio Mw/Mn.

The standard density (SD), expressed in kg/m$^3$, was measured in accordance with the standard ISO 1183-3 (1999).

The productivity is defined as the quantity of polyolefin obtained in kg per mmol of transition metal during one hour of polymerization.

Example 1

Synthesis of {2,6-bis(1-(2-Methyl-1-naphthylimino) ethyl]pyridine-κ$^3$:N,N',N"}FeCl$_2$ (Compound 1).

a) Synthesis of 1-Amino-2-methylnaphthalene 10 g (53.42 mmol) of 2-methyl-1-nitronaphthalene dissolved in 125 ml of methanol and 0.57 g (0.057 g of Pd, 0.54 mmol) of palladium on activated charcoal were introduced successively into an autoclave.

The suspension was heated to 50° C. during 4 hours under a pressure of 10×10$^5$ Pa of hydrogen, then filtered at ambient temperature. The solution obtained was evaporated and distilled in vacuo. This gave 6.7 g of 1-amino-2-methylnaphthalene in the form of a yellow oil with a boiling point of between 145 and 150° C. at 133.3 Pa.

$^1$H NMR (CDCl$_3$–300K–500 MHz) δ=2.40 (s, 3H, —C$\underline{H}_3$), 4.15 (s, broad, 2H, —N$\underline{H}$2), 7.33 (d, 2H, H$_{3\ naphth}$, $^3$J$_{H3\text{-}H4}$~8 Hz), 7.28 (d, 2H, H$_{2\ naphth}$), 7.47 (m 2H, H$_{6\text{-}7\ naphth}$) 7.82 (m, 2H, H$_{8\text{-}5\ naphth}$) in ppm.

b) Synthesis of 2,6-bis(1-(2-Methyl-1-naphthylimino)ethyl]pyridine.

1.20 g (7.35 mmol) of 2,6-diacetylpyridine dissolved in 25 ml of ethanol were introduced into a 100 ml round-bottomed flask under nitrogen, with stirring.

3.0 g (20.25 mmol) of 1-amino-2-methylnaphthalene dissolved in 10 ml of ethanol were then added dropwise, followed by 0.1 ml of glacial acetic acid. The mixture was heated at reflux for 18 hours, with stirring, then cooled to ambient temperature and dried in vacuo so as to obtain crude 2,6-bis[1-(2-methyl-1-naphthylimino)-ethyl]pyridine, which was dissolved in methylene chloride and neutralized with an aqueous solution of sodium carbonate. The organic phase was separated, and 100 ml of water were added thereto. After dewatering and evaporation of the organic phase, the 2,6-bis[1-(2-methyl-1-naphthylimino)ethyl] pyridine was purified by liquid chromatography on a silica column using a 25/75 v/v AcOEt/n-hexane mixture as eluent. This gave 1.33 g of yellow microcrystalline solid.

$^1$H NMR (CDCl$_3$–300K–500 MHz) δ=2.26 (m, 12H, —C$\underline{H}_3$ imine and —C$\underline{H}_3$ $_{naphthyl}$), 7.45 (m, 6H, H$_{5\text{-}6\text{-}7\ naphth}$), 7.58 (d, 2H, H$_{8\ naphth}$ $^3$J$_{H7\text{-}H8}$~8 Hz), 765 (d, 2H, H$_{3\ naphth}$, $^3$J$_{H3\text{-}H4}$~8 Hz), 7.85 (d, 2H, H$_{4\ naphth}$) 8.06 (t, 1H, H$_{p\ py}$, $^3$J$_{Hm\text{-}Hp}$~8 Hz), 8.68 (d, 2H, H$_{m,\ py}$, $^3$J$_{Hm\text{-}Hp}$~8 Hz) in ppm. FTIR (KBr pressing) ν=1640 (ν$_{C=N}$) imine) in cm$^{-1}$ c) Synthesis of Compound 1.

186 mg (1.467 mmol) of activated ferrous chloride were introduced under nitrogen into a 100 ml round-bottomed flask, followed by 10 ml of anhydrous THF (tetrahydrofuran) and by a solution of 665 mg (1.506 mmol) of 2,6-bis[1-(2-methyl-1-naphthylimino)-ethyl]pyridine in 25 ml of THF.

This last addition caused instantaneous formation. of a blue-grey precipitate. The mixture was then heated at reflux for 18 hours, with stirring.

Once the mixture had been cooled to ambient temperature, the solid was finally filtered under nitrogen, rinsed with hexane and dried in vacuo.

This gave 610 mg of compound 1.

Elemental analysis: C=64.2 (theory (th.) 65.5); N=7.3 (th. 7.4); H=4.9 (th. 4.8); Fe=(th. 9.8); Cl=13.0 (th. 12.5) % w/w.

Example 2

Synthesis of {2,6-bis[1-(2-Methyl-1-naphthylimino) methyl]pyridine-κ$^3$:N,N',N"}FeCl2 (Compound 2).

a) Synthesis of 2,6-bis[(2-Methyl-1-naphthylimino)-methyl] pyridine.

Step b of Example 1 was repeated, but using 1.00 g (7.41 mmol) of 2,6-diformylpyridine and 3.2 g (22.35 mmol) of 1-amino-2-methylnaphthalene dissolved in 20 ml of ethanol, without adding glacial acetic acid during mixing, and purifying with a 20/80 AcOEt/n-hexane mixture as eluent. This gave 890 mg of a golden yellow solid.

$^1$H NMR (CDCl$_3$–300K–500 MHz) δ=2.40 (s, 6H, —C$\underline{H}_3$ $_{naphthyl}$) 7.42 (m, 6H, H$_{naphth}$), 7.62 (d, 2H, H$_{naphth}$), 7.85 (m, 4H, H$_{naphth}$), 8.11 (t, 1H, H$_{p\ py}$, $^3$J$_{Hm\text{-}Hp}$~7 Hz), 8.62 (d, 2H, H$_{m\ py}$, $^3$J$_{Hm\text{-}Hp}$~8 Hz), 8.80 (s, 2H, H$_{iminoformyl}$) in ppm.

b) Synthesis of Compound 2.

Step c of Example 1 was repeated, but using 180 mg of activated ferrous chloride and 600 mg of 2,6-bis[(2-methyl-1-naphthylimino)methyl]pyridine. This last addition was seen to cause instantaneous formation of a beige-coloured precipitate. 630 mg of compound 2 were obtained. Elemental analysis: C=63.8 (th. 64.5); N=7.7 (th. 7.8); H=4.5 (th. 4.3); Fe=(th. 10.3); Cl=12.4 (th. 13.1) % w/w.

Example 3

Synthesis of {2,6-bis[1-(1-Anthracenylimino)ethyl]pyridine-κ$^3$:N,N',N")FeCl$_2$ (Compound 3).

a) Synthesis of 2,6-bis[1-(1-Anthracenylimino) Ethyl]-pyridine 0.70 g (4.29 mmol) of 2,6-diacetylpyridine dissolved in 40 ml of ethanol were introduced under nitrogen into a 250 ml round-bottomed flask. The mixture was heated at reflux and stirred.

2.5 g of 1-aminoanthracene (purchased from Aldrich) dissolved in 80 ml of ethanol were then added dropwise, followed by 0.2 ml of glacial acetic acid.

After 60 hours of stirring at reflux, the mixture was cooled to ambient temperature; the solid was filtered and dried in vacuo, giving 2.1 g of 2,6-bis[1-(1-anthracenylimino)ethyl]pyridine in the form of a yellow powder.

$^1$H NMR (CDCl$_3$–300K–500 MHz) δ=2.50 (s, 6H, —C$\underline{H}_3$), 6.84 (d, 2H, H$_{2\ anthr}$, $^3J_{H2-H3}$~7 Hz), 7.48 (m, 6H, H$_{anthr}$), 7.84 (d, 2H, H$_{anthr}$), 7.99 (d, 2H, H$_{anthr}$), 8.03 (d, 2H, H$_{anthr}$), 8.12 (t, 1H, H$_{p\ py}$, $^3J_{Hm-Hp}$~8 Hz), 8.41 (s, 2H, H$_{anthr}$), 7.49 (s, 2H, H$_{anthr}$), 8.75 (d, 2H, H$_{m\ py}$, $^3J_{Hm-Hp}$~8 Hz) in ppm.

FTIR (KBr pressing) ν=1635 (ν$_{C=N}$ imine) in cm$^{-1}$.

b) Synthesis of Compound 3.

240 mg (1.893 mmol) of activated ferrous chloride, 10 ml of anhydrous THF and 50 ml of a solution of 1.00 g (1.948 mmol) of 2,6-bis[1-(1-anthracenylimino)ethyl]pyridine in THF were introduced successively under nitrogen into a 100 ml round-bottomed flask.

This last addition caused an instantaneous change in the colour of the solution, which became green. The mixture was then heated for 3 hours at reflux, with stirring.

Once the mixture had been cooled to ambient temperature and the THF had been evaporated in vacuo, a green residue was obtained, which was suspended in hexane, with stirring; the solid was then filtered under nitrogen, rinsed with hexane and dried in vacuo. This gave 905 mg of compound 3.

Elemental analysis: C=67.6 (th. 69.4); N=6.1 (th. 6.6); H=4.7 (th. 4.2); Fe=(th. 8.7); Cl=10.9 (th. 11.1) % w/w.

Example 4

Synthesis of {2,6-bis[1-(1-Anthracenylimino)methyl]pyridine-κ$^3$:N,N',N"}FeCl$_2$ (compound 4)

a) Synthesis of 2,6-bis[(-1-Anthracenylimino)methyl]pyridine.

0.50 g (3.704 mmol) of 2,6-diformylpyridine dissolved in 25 ml of ethanol were introduced under nitrogen into a 100 ml round-bottomed flask. The mixture was heated to reflux and stirred.

2.15 g (11.11 mmol) of 1-aminoanthracene (provided by Aldrich) dissolved in 45 ml of ethanol were then added dropwise.

After 45 hours of stirring at reflux, the mixture was cooled to ambient temperature; the solid was filtered and dried in vacuo, giving 1.68 g of 2,6-bis[(1-anthracenylimino)methyl]pyridine in the form of a yellow solid.

$^1$H NMR (CDCl$^3$–300K–500 MHz) δ=7.15 (d, 2H, H$_{2anthr}$, $^3J_{H2-H3}$~7 Hz), 7.50 (m, 6H, H H$_{anthr}$), 7.95 (d, 2H, H H$_{3anthr}$), 8.08 (m, 4H, H$_{anthr}$), 8.13 (t, 1H, H$_{p\ py}$, $^3J_{Hm-Hp}$~8 Hz), 8.48 (s, 2H, H$_{5\ or\ 10\ anthr}$), 8.65 (d, 2H, H$_{m\ py}$, $^3J_{Hm-Hp}$~8 Hz), 8.90 (s, 2H, H$_{iminoformyl}$), 8.95 (s, 2H, H$_{5\ or\ 10\ anthr}$) in ppm.

b) Synthesis of Compound 4.

254 mg (2.004 mmol) of activated ferrous chloride and then 10 ml of anhydrous THF followed by a solution of 1.012 g (2.085 mmol) of 2,6-bis[1(1-anthracenylimino) methyl]pyridine in 75 ml of THF were introduced under nitrogen into a 100 ml round-bottomed flask.

This last addition caused instantaneous formation of a mauve-coloured precipitate. The mixture was then heated for 18 hours at reflux, with stirring.

Once the mixture had been cooled to ambient temperature and the THF had been evaporated in vacuo, a mauve residue was obtained, which was then suspended in hexane, with stirring; the solid was finally filtered under nitrogen, rinsed with hexane and dried in vacuo. This gave 1.155 g of compound 4.

Elemental analysis: C=68.4 (th. 68.7); N=6.2 (th. 6.9); H=5.2 (th. 3.8); Fe=(th. 9.1); Cl=10.0 (th. 11.6) % w/w.

Examples 5 to 8

Ethylene Polymerizations

The ethylene polymerization experiments were conducted in a steel autoclave (AC) of 5 litres internal volume. At the outset, the autoclave was charged with MAO (10% by weight solution in toluene, EURECENE® T5010 grade marketed by the company Witco) observing the Al/Fe ratio given in Table 1, and the autoclave was charged with 2.0 litres of isobutane and then heated to 50° C. Ethylene was then introduced into the autoclave until the partial pressure was 10×10$^5$ Pa.

The quantity mentioned in Table 1 of the complex prepared in Examples 1 to 4 was introduced under anhydrous nitrogen into a 50 ml round-bottomed flask. The quantity of MAO necessary to obtain an atomic ratio Al/Fe of 1000 in precontact was then added to the flask under nitrogen. The catalytic solution was then immediately introduced into the autoclave tube under argon.

0.5 litre of isobutane were then used to drive the catalyst from the tube into the autoclave; stirring of the autoclave was maintained at the specified temperature and pressure for one hour. The polymer was obtained after isobutane degassing The polymerization conditions and the characteristics of the polymers obtained are found in Table 1 below.

Example 9

Copolymerization of Ethylene with 1-hexene

The operations of Example 7 were repeated, but adding 50 ml of 1-hexene with ethylene to the autoclave, using 5 μmol of the complex prepared in Example 3, and with a total Al/Fe ratio of 2000.

Example 10R (non-Inventive)

The operations of Example 6 or 8 were repeated, but using 5 μmol of the complex {2,6-bis[1-(1-naphthylimino)methyl}pyridine-κ$^3$:N,N',N"}FeCl$_2$ (DIPNaphthFeCl$_2$). The characteristics of the polyethylene obtained are found in Table 1 below and show that this complex gives both low productivity and low molecular weight.

Example 11R (non-Inventive)

The operations of Example 6 or 8 were repeated, but using 5 μmol of the complex {2,6-bis[1-(2,4,6-trimethyl-1-phenylimino)ethyl}pyridine-κ$^3$:N,N',N"}FeCl$_2$ (MeDIP2,4,6MePhFeCl$_2$), prepared as described by Britovsek et al. in J. Am. Chem. Soc., 1999, 121, 8728) and n-hexane as solvent. The characteristics of the polyethylene obtained are found in Table 1 below and show that this complex gives polyethylene with no ethyl or butyl branching.

Examples 12 to 20

Ethylene Copolymerizations in Liquid Propylene

The autoclave was charged with the quantity of MAO necessary to attain an atomic Al/Fe ratio of 4000, and after 1.0 liter of liquid propylene had been added at ambient temperature, the autoclave was heated to the specified temperature (30 or 50° C.). Ethylene is introduced at the specified temperature into the autoclave until the molar $C_2/C_3$ ratio intended is reached in the gaseous phase. 5 μmol of the complex prepared in Example 1 or 3 were introduced into a 50 ml round-bottomed flask under anhydrous nitrogen. The quantity of MAO necessary to attain an atomic Al/Fe ratio of 1000 in precontact was then added to the flask. The catalytic solution was introduced immediately into the tube of the autoclave, under argon.

0.5 litre of propylene were then used to drive the catalyst from the tube into the autoclave; stirring of the autoclave was maintained at the specified temperature and pressure for one hour, adding ethylene so as to keep the $C_2/C_3$ ratio constant. The polymer was obtained after propylene degassing.

The polymerization conditions and the characteristics of the polymers obtained are found in Tables 2 (compound 1) and 3 (compound 3) below.

Examples 21R and 22R (non-Inventive)

The operations of Examples 18 and 20 were repeated, respectively, but using {2,6-bis[1-(2,6-diisopropyl-1-phenylimino)ethyl]pyridine-$\kappa^3$:N,N',N")FeCl$_2$ (MeDIP2, 6iPrPhFeCl$_2$), prepared as described in WO98/30612 as complex. The results are given in Table 3 and show that the rate of incorporation of propylene is clearly inferior to that obtained with the complexes of the invention.

TABLE 2

| Example | Unit | 12 | 13 | 14 | 15 |
|---|---|---|---|---|---|
| Polymerization | | | | | |
| Complex (a) | — | Ex.1 | Ex.1 | Ex.1 | Ex.1 |
| Temperature | ° C. | 50 | 30 | 50 | 30 |
| $C_2/C_3$ (AC) | % mol/mol | 8 | 7 | 20 | 24 |
| Productivity | kg/mmol Fe.hour | 33.8 | 50.0 | 138.8 | 181.0 |
| Characteristics | | | | | |
| Mw | daltons | 7354 | 4884 | 11481 | 7593 |
| Mw/Mn | — | 1.93 | 1.7 | 2.17 | 2.17 |
| Rate of $C_3$ incorporation | % w/w | 17 | 30 | 11 | 23 |
| Molar fraction of triads | | | | | |
| EEE | + EEP | — | 0.681 | 0.358 | 0.779 0.57 |
| PEE | — | 0.188 | 0.36 | 0.138 | 0.247 |
| PEP | | — | 0.006 | 0.019 | 0.002 0.011 |
| EPE | + PPE | — | 0.077 | 0.154 | 0.056 0.108 |
| EPP | — | 0.043 | 0.091 | 0.031 | 0.053 |
| PPP | | — | 0.004 | 0.019 | 0.005 0.011 |

TABLE 1

| | | Example | | | | | | |
|---|---|---|---|---|---|---|---|---|
| | Unit | 5 | 6 | 7 | 8 | 9 | 10R | 11R |
| Polymerization | | | | | | | | |
| Complex (a) | — | Ex. 1 | Ex. 2 | Ex. 3 | Ex. 4 | Ex.3 | DIPNaphFeCl$_2$ | MeDIP2,4,6,MePhFeCl$_2$ |
| Complex (a) | μmol | 1 | 5 | 1 | 5 | 5 | 5 | 5 |
| Al/Fe | mol/mol | 4000 | 2000 | 4000 | 2000 | 2000 | 2000 | 2000 |
| 1-Hexene | ml | 0 | 0 | 0 | 0 | 50 | 0 | 0 |
| Productivity | kg/mmol Fe.hour | 485 | 9.8 | 537 | 3.1 | 252 | 2 | 100 |
| Characteristics | | | | | | | | |
| SD | kg/m$^3$ | 971.4 | — | — | — | — | — | — |
| Mw | 10$^3$ daltons | 136 | 121 | 1.5 | 68 | 1.3 | 2.9 | 259 |
| mp | ° C. | 133.7 | 129.8 | 116.7 | 129.8 | 95.3 | 112 | 134 |
| ΔHm | J/g | 275 | 249 | 151 | 193 | — | 148 | 228 |
| Ethyl branching | Number/1000 C | <0.5 | <0.5 | 2.7 | 0.8 | 2.5 | 0.9 | 0 |
| Butyl branching | Number/1000 C | 0 | 0 | 0.2 | 0 | 1.2 | 0 | 0 |
| 1-Butene | g/kg | <2 | <2 | 10 | 3 | 10 | 4 | 0 |
| 1-Hexene | g/kg | 0 | 0 | 0 | 0 | 7.13 | 0 | 0 |

TABLE 3

| | Unit | Example | | | | | | |
|---|---|---|---|---|---|---|---|---|
| | | 16 | 17 | 18 | 19 | 20 | 21R | 22R |
| Polymerization | | | | | | | | |
| Complex (a) | — | Ex. 3 | Ex. 3 | Ex. 3 | Ex. 3 | Ex. 3 | MeDIP2, 6iPrPhFeCl$_2$ | MeDIP2, 6iPrPhFeCl$_2$ |
| Temperature | ° C. | 50 | 50 | 30 | 30 | 50 | 30 | 50 |
| C$_2$/C$_3$ (AC) | % mol/mol | 28 | 14 | 16 | 7 | 8 | 14 | 9 |
| Productivity | kg/mmol Fe.hour | 45.6 | 30.6 | 132.0 | 95.4 | 15.2 | 21.1 | 6.4 |
| Characteristics | | | | | | | | |
| Mw | daltons | 3291 | 1436 | 1379 | 1252 | 1049 | 279400 | 203700 |
| Mw/Mn | — | 2.62 | 1.48 | 1.42 | 1.45 | 1.3 | 13 | 18 |
| Rate of C$_3$ incorporation | % w/w | 12 | 19 | 44 | 54 | 28 | 0.6 | 0.4 |
| Molar fraction of triads | | | | | | | | |
| EEE | — | 0.742 | 0.69 | 0.295 | 0.179 | 0.486 | — | — |
| PEE + EEP | — | 0.131 | 0.165 | 0.323 | 0.328 | 0.258 | — | — |
| PEP | — | 0.003 | 0.005 | 0.008 | 0.012 | 0.011 | — | — |
| EPE | — | 0.031 | 0.04 | 0.067 | 0.075 | 0.045 | — | — |
| EPP + PPE | — | 0.075 | 0.095 | 0.204 | 0.203 | 0.192 | — | — |
| PPP | — | 0.018 | 0.005 | 0.103 | 0.203 | 0.008 | — | — |

What is claimed is:

1. A complex of a transition metal having formula (I)

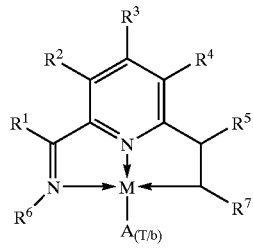

wherein

M is a transition metal of groups 6 to 12,

T is the oxidation state of M, each A, which may be identical with or differ from each other, is an atom or an atomic grouping bonded covalently or ionically to the transition metal M, b is the valency of A, each $R^1$, $R^2$, $R^3$, $R^4$ and $R^5$ is independently a hydrogen atom, an unsubstituted or substituted hydrocarbon group, an unsubstituted or substituted heterohydrocarbon group, or an inert functional group, and $R^6$ and $R^7$ are, independently of one another, a polynuclear aromatic hydrocarbon group containing at least two condensed benzene nuclei, substituted with at least one hydrocarbon group.

2. The complex according to claim 1, wherein M is Fe, Cr, Co, Ru or Mn.

3. The complex according to claim 1 or 2, wherein T is 2.

4. The complex according to claim 1 wherein A is a halogen atom.

5. The complex according to claim 1 wherein $R^1$ and $R^5$ are independently a linear or branched alkyl group containing from 1 to 6 carbon atoms.

6. The complex according to claim 1, wherein $R^6$ and $R^7$ comply independently of each other with the formulae (II) or (III) below:

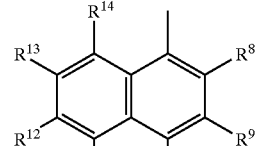

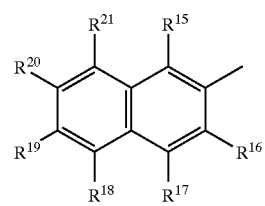

wherein $R^8$ to $R^{21}$ are independently hydrogen atoms or hydrocarbon groups, such that at least two thereof can form a ring, with the proviso that at least one of the groups selected from $R^8$ to $R^{14}$ is not a hydrogen atom.

7. The complex according to claim 6, wherein $R^6$ and $R^{71}$ are represented by the formula (II).

8. The complex according to claim 7, wherein $R^1$ and $R^5$ are a linear or branched alkyl group containing from 1 to 6 carbon atoms and $R^8$ is a linear or branched alkyl group containing from 1 to 8 carbon atoms.

9. A process for polymerizing alpha-olefins, comprising:
polymerizing at least one alpha-olefin in the presence of a catalytic system comprising
(a) a complex according to claim 1 and
(b) at least one activator, thereby obtaining a polymer.

10. The process for polymerizing alpha-olefins according to claim 9, wherein the activator is selected from the group consisting of aluminoxanes and trialkylaluminium compounds.

11. The process according to claim 9 or 10, wherein said polymer is a homopolymer or a copolymer of ethylene.

12. Copolymers of ethylene which optionally contain up to 99% by weight of monomeric units derived from propylene, and which are capable of manufacture according to claim 9 or 10.

13. The process according to claim 9, wherein M in said complex is Fe, Cr, Co, Ru or Mn.

14. The process according to claim 9, wherein T in said complex is 2.

15. The process according to claim 9, wherein A in said complex is a halogen atom.

16. The process according to claim 9, wherein $R^1$ and $R^5$ in said complex are independently a linear or branched alkyl group containing from 1 to 6 carbon atoms.

17. The process according to claim 9, wherein
$R^6$ and $R^7$ in said complex comply independently of each other with the formulae (II) or (III) below:

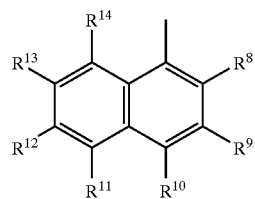

(II)

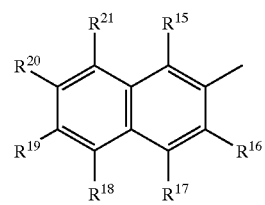

(III)

wherein $R^8$ to $R^{21}$ are independently hydrogen atoms or hydrocarbon groups, such that at least two thereof can form a ring, with the proviso that at least one of the groups selected from $R^8$ to $R^{14}$ is not a hydrogen atom.

18. The process according to claim 9, wherein $R^6$ and $R^7$ in said complex are represented by the formula (II).

19. process according to claim 9, wherein $R^1$ and $R^5$ in said complex are linear or branched alkyl group containing from 1 to 6 carbon atoms and $R^8$ is a linear or branched alkyl group containing from 1 to 8 carbon atoms.

* * * * *